United States Patent
Receveur

(10) Patent No.: US 9,132,268 B2
(45) Date of Patent: Sep. 15, 2015

(54) MINIATURIZED FEEDTHROUGH

(75) Inventor: Rogier Receveur, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 1244 days.

(21) Appl. No.: 11/948,673

(22) Filed: Nov. 30, 2007

(65) Prior Publication Data
US 2008/0140148 A1  Jun. 12, 2008

Related U.S. Application Data

(60) Provisional application No. 60/868,007, filed on Nov. 30, 2006.

(51) Int. Cl.
*A61N 1/375* (2006.01)
*A61N 1/05* (2006.01)

(52) U.S. Cl.
CPC ............... *A61N 1/05* (2013.01); *A61N 1/3754* (2013.01)

(58) Field of Classification Search
CPC ... A61N 1/3754; A61N 1/3752; A61N 1/375; A61N 1/3758; Y10S 439/909; H01G 4/35
USPC ......... 607/36, 37; 600/300; 422/58; 361/313; 361/302; 439/909; 257/698; 174/650–665
See application file for complete search history.

(56) References Cited

U.S. PATENT DOCUMENTS

| | | | |
|---|---|---|---|
| 5,564,434 A | 10/1996 | Halperin | |
| 5,683,758 A * | 11/1997 | Evans et al. | 427/555 |
| 5,750,926 A | 5/1998 | Schulman | |
| 7,068,491 B1 * | 6/2006 | Burdon et al. | 361/313 |
| 7,164,572 B1 | 1/2007 | Burdon | |
| 2001/0039374 A1 * | 11/2001 | Schulman | 600/300 |
| 2004/0061234 A1 * | 4/2004 | Shah et al. | 257/758 |
| 2004/0186542 A1 | 9/2004 | Van Venrooij | |
| 2004/0223875 A1 * | 11/2004 | Pendo et al. | 422/58 |
| 2006/0009813 A1 * | 1/2006 | Taylor et al. | 607/36 |
| 2006/0241731 A1 | 10/2006 | Receveur | |
| 2007/0158769 A1 | 7/2007 | You | |

FOREIGN PATENT DOCUMENTS

| | | | |
|---|---|---|---|
| EP | 1400993 A | 3/2004 | |
| WO | 02102267 A | 12/2002 | |
| WO | 03023388 A | 3/2003 | |

OTHER PUBLICATIONS

International Search Report, PCT/US2007/086042, Jun. 24, 2008, 6 Pages.

* cited by examiner

*Primary Examiner* — Tammie K Heller
(74) *Attorney, Agent, or Firm* — Carol F. Barry

(57) ABSTRACT

Formation of a feedthrough in a substrate for use in an implantable medical device is presented. A substrate includes a first surface and a second surface, and a via that extends through the first and the second surfaces. A dielectric layer is formed over one of a first surface of the substrate. Conductive material is introduced into the via to form a feedthrough.

25 Claims, 19 Drawing Sheets

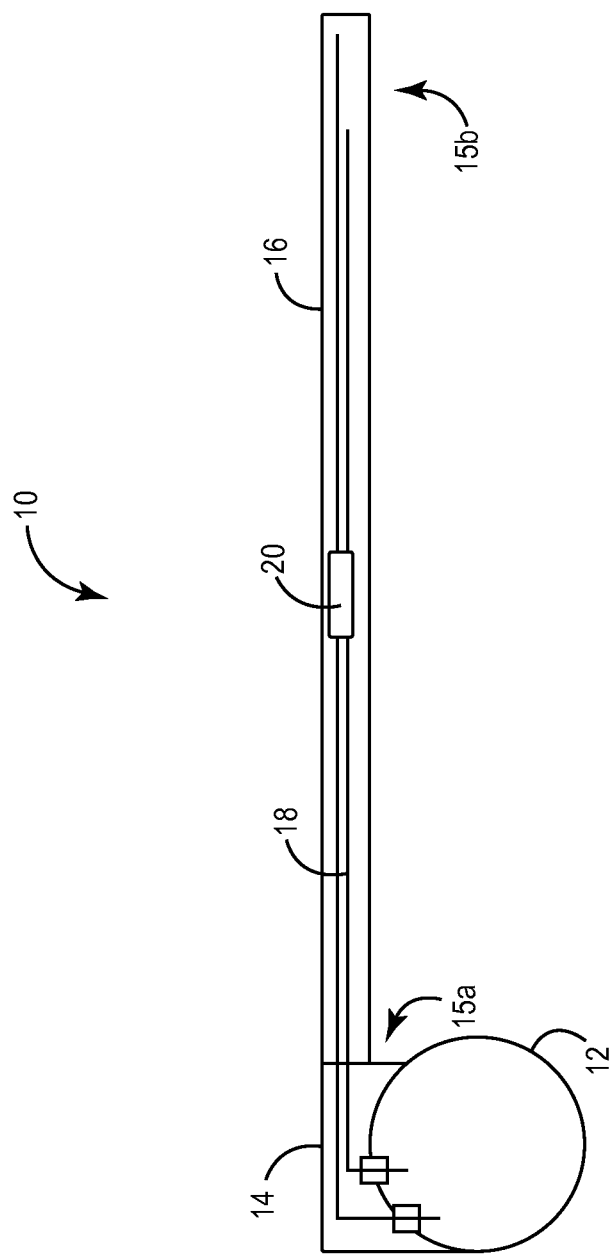

ND FEEDTHROUGH

MINIATURIZED FEEDTHROUGH

RELATED APPLICATIONS

The present application claims priority and other benefits from U.S. Provisional Patent Application Ser. No. 60/868,007 filed Nov. 30, 2006, incorporated herein by reference in its entirety.

FIELD OF THE INVENTION

The present invention relates generally to an implantable medical device (IMD) and, more particularly, to formation of a miniaturized feedthrough in a substrate associated with the IMD.

BACKGROUND OF THE INVENTION

Numerous devices (e.g., implantable medical devices (IMDs), electrochemical cells (e.g. batteries, capacitors etc.), sensors etc.) are hermetically sealed to prevent liquid from contacting electronic components within the device. A typical feedthrough assembly consists of a conductive element (e.g., wires etc.), a ferrule, an insulator member (e.g. glass, ceramic etc.), and a seal. The ferrule includes an aperture configured to receive the insulator member. A seal is located between the ferrule and the insulator member. An exemplary feedthrough assembly may be inserted, for example, into a housing of a battery such that a portion of the conductive element extends into the housing to connect with battery elements while another portion of the conductive element extends outside of the housing to connect with other electronic components. It is desirable to develop new feedthroughs for IMDs.

BRIEF DESCRIPTION OF THE DRAWINGS

The present invention will become more fully understood from the detailed description and the accompanying drawings, wherein:

FIG. 1 depicts a schematic view of an implantable medical device;

DETAILED DESCRIPTION

Figure 2A:
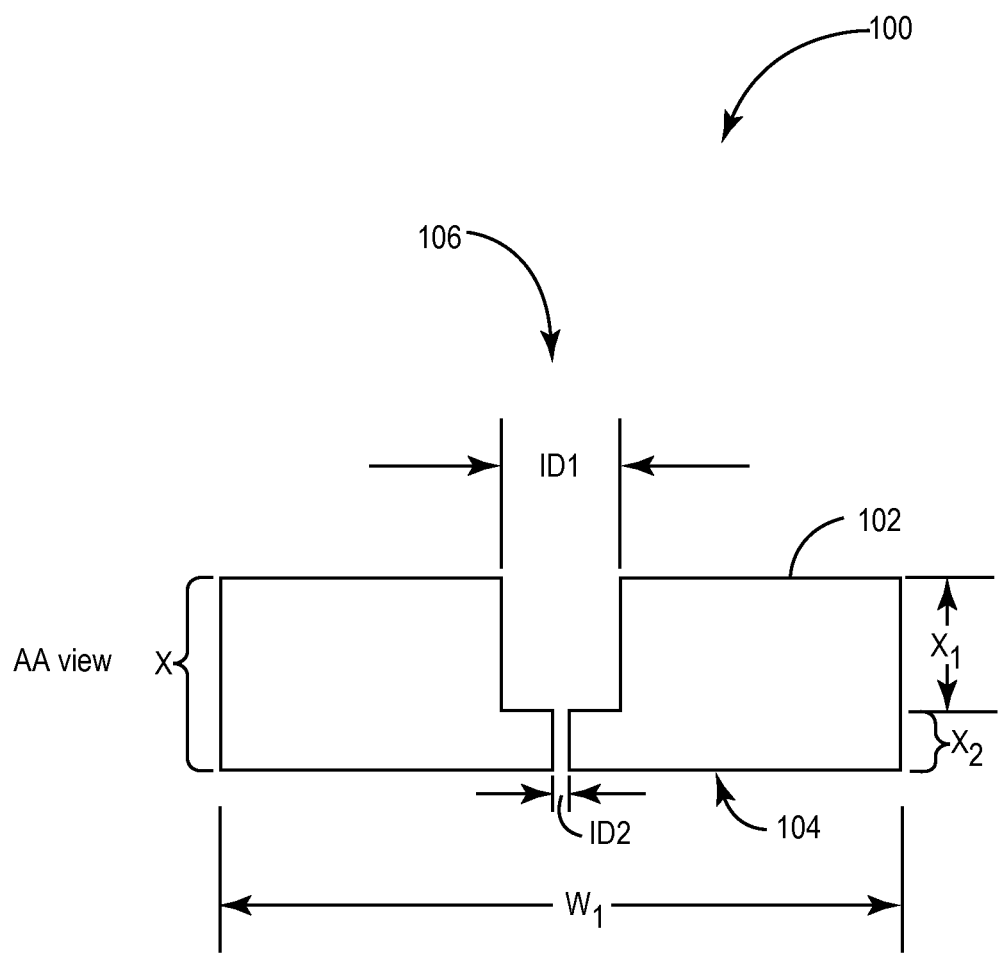
FIG. 2A depicts a schematic cross-sectional view of a substrate.

The following description of an embodiment is merely exemplary in nature and is in no way intended to limit the invention, its application, or uses. For purposes of clarity, the same reference numbers are used in the drawings to identify similar elements.

One embodiment of the present invention is directed to formation of a miniaturized feedthrough in a sensor substrate for an implantable medical device (IMD). The substrate has a first surface and a second surface with a via that extends therethrough. A dielectric layer is introduced or formed over the first surface of the substrate. Temporarily, a holding device is coupled to the first surface of the substrate such that the dielectric layer is disposed between the first surface of the substrate and the holding device. A conductive material is introduced into the via to form a miniaturized or chip scale feedthrough. Thereafter, the holding device and dielectric layer are removed from the first surface of the substrate. The feedthrough can then be electrically connected to another electronic component or device.

FIG. 1 depicts a functional unit 20 in a medical device system 10. Functional unit 20 includes a miniaturized feedthrough (not shown) on an integrated circuit (IC), a substrate that includes electronic components (e.g. transistors, logic gates, switches etc.), or a substrate alone. Functional unit 20 can be used anywhere outside the medical device 12 and is electrically connected to one or more conductor(s) 18. For example, functional unit 20 serves as a sensor that employs a miniaturized feedthrough. Medical device system 10 includes a medical device housing 12 having a connector module 14 that electrically couples various internal electrical components of medical device housing 12 to a proximal end 15a of a medical lead 16 such as one or more conductors 18 (e.g. coil, wire etc.) that extend to a distal end 15b of lead 16. Medical device system 10 may comprise any of a wide variety of medical devices that include one or more medical lead(s) 16 and circuitry coupled to the medical lead(s) 16. By way of example, medical device system 10 may take the form of an implantable cardiac pacemaker that provides therapeutic stimulation to the heart or a neurostimulator. Alternatively, medical device system 10 may take the form of an implantable cardioverter, an implantable defibrillator, an implantable cardiac pacemaker-cardioverter-defibrillator (PCD), an implantable pulse generator, or an implantable medical device that solely monitors conditions associated with the patient.

FIGS. 2A through 2J illustrate one embodiment in which feedthrough 109 is formed in an aperture 106 of a substrate 100. Substrate 100 is a body or base layer of an IC onto which other layers are deposited to form the circuit. Substrate 100 includes electronic components that allow substrate 100 to function as a sensor substrate; however, skilled artisans appreciate that the substrate may be configured to include any type of circuitry such as switches, signal processing capability, and/or any other suitable form of circuitry related to an implantable medical device. In one embodiment, substrate 100 comprises a semiconductor such as a silicon wafer (e.g. single crystal, or other crystal orientation), silicon-on-insulator substrates, sapphire, and/or nonsilicon substrates (e.g. ceramic, metal, polymer, etc.). Substrate 100 includes first and second surfaces 102, 104, a width (W1), a height (X) and a depth (D1).

An aperture 106 is formed in substrate 100 that extends through the first and second surfaces 102, 104. Aperture 106 has a first inner diameter (ID1) that extends a first distance X1 from the first surface 102 and a second inner diameter (ID2) that extends a second distance X2 from the second surface 104 to X1. The total length X of aperture 106 is equivalent to X1+X2. Exemplary dimensions of substrate 100 and aperture 106 include W1 of about 1000 micrometers (um), X of about 250 um, X1 of about of about 180 um, X2 of about 70 um, a depth D1 of about 1000 um, ID1 of about 180 um and ID2 about 70 um; however, other sizes of substrate 100 and aperture 106 may also be used.

Figure 2B:
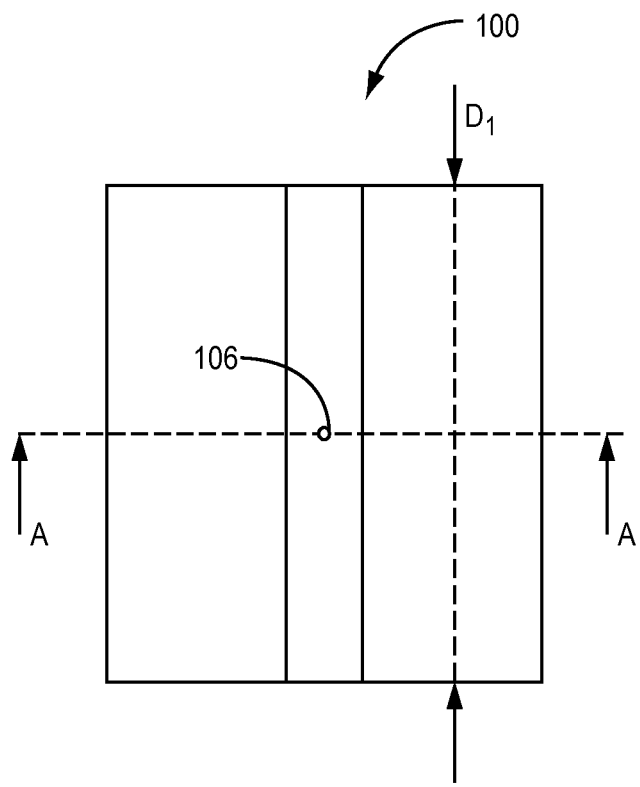
FIG. 2B depicts a top view of the substrate depicted in FIG. 2A.
Figure 2C:
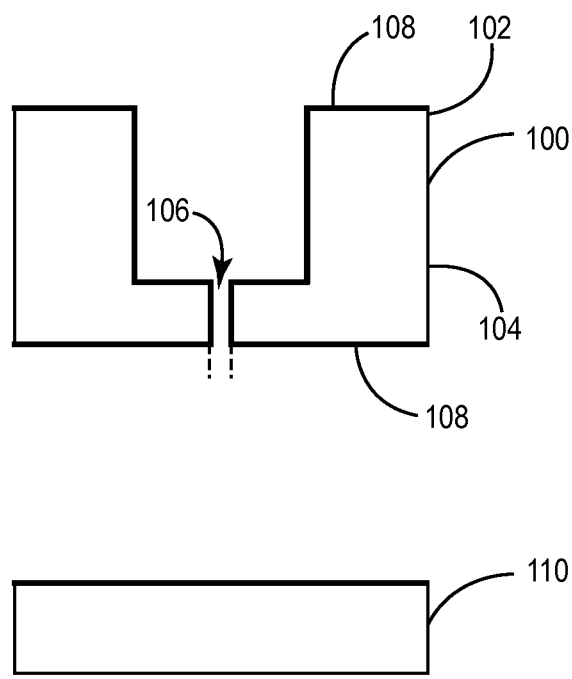
FIG. 2C depicts an insulative layer formed in a first and a second surface of the substrate with a holding device near the substrate.

Aperture 106 is formed through mechanical and/or chemical means, as shown in FIGS. 2A-2C. At least one or both of first and second surfaces 102 and 104 include a mask (not shown) and insulative layer 108 (e.g. silicon dioxide ($SiO_2$) etc.) in which aperture 106 is anisotropically etched by, for example, a dry reactive ion etcher (DRIE) to a depth of about X1 on the first surface 102 whereas the mask on second surface 104 is anisotropicaly etched to a depth of about X2 with an ID2. This two sided approach for forming aperture 106 allows for a smaller ID2 along with a smaller X1 to be created which reduces the aspect ratio of aperture 106.

Figure 2D:
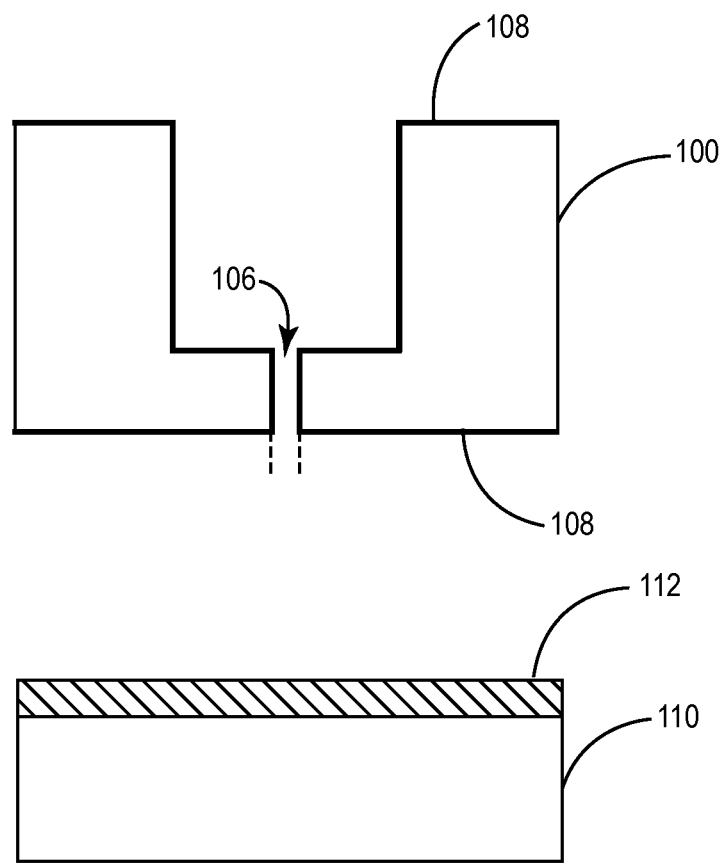
FIG. 2D depicts a plating base over the holding device of FIG. 2C.
Figure 2E:
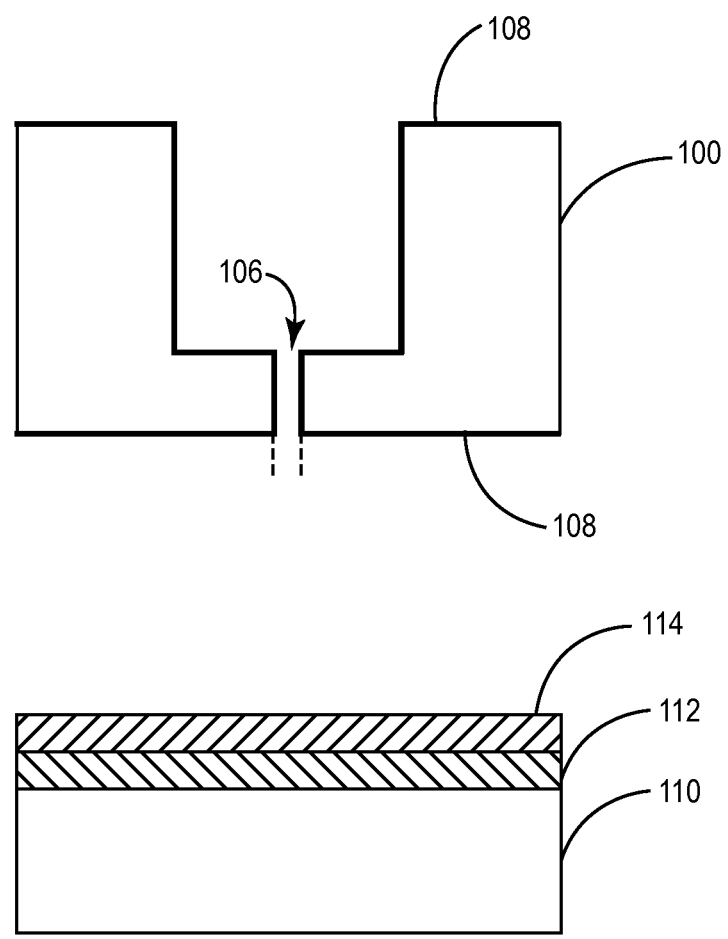
FIG. 2E depicts a dielectric layer disposed over the plating base in FIG. 2D.
Figure 2F:
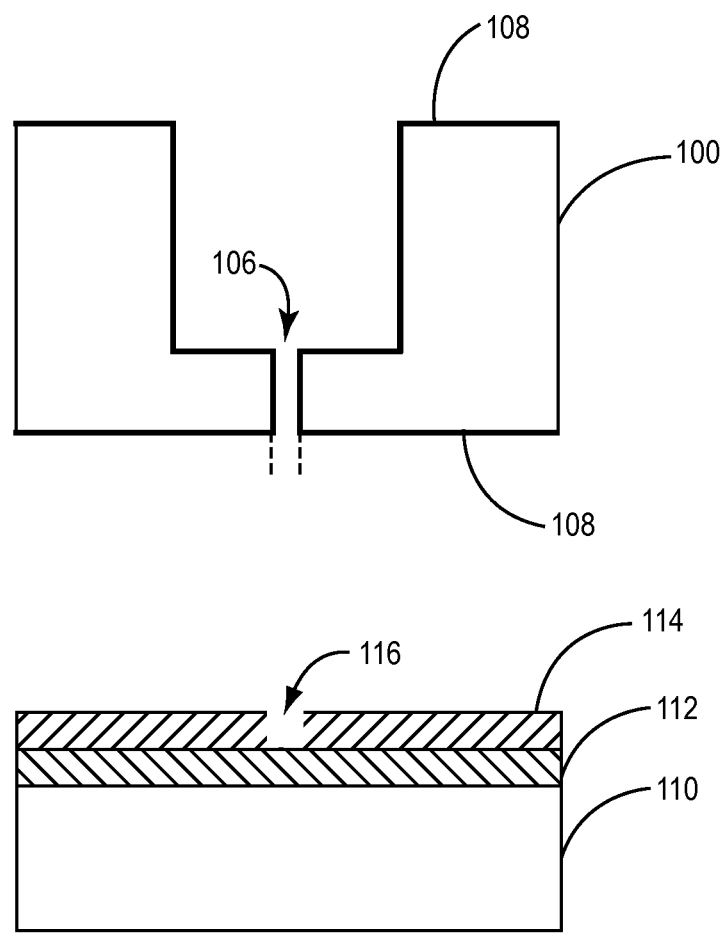
FIG. 2F depicts a via formed in the dielectric layer of FIG. 2E.
Figure 2G:
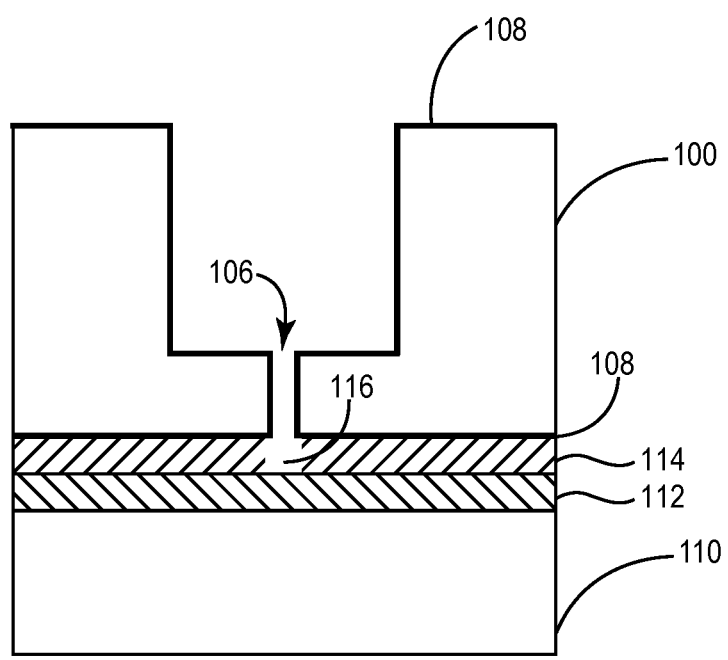
FIG. 2G depicts the substrate coupled to the holding device.
Figure 2H:
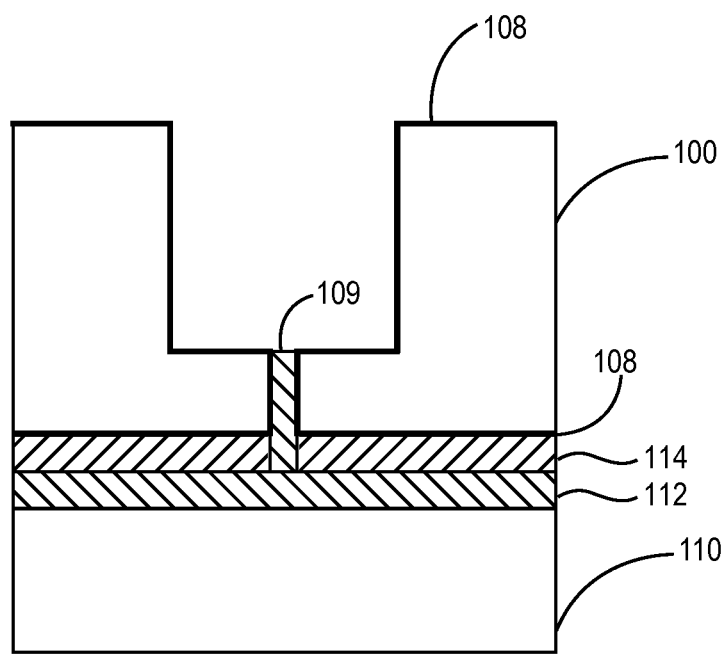
FIG. 2H depicts conductive material introduced over the vias of the substrate and the dielectric layer in order to form the feedthrough in the substrate.
Figure 2I:
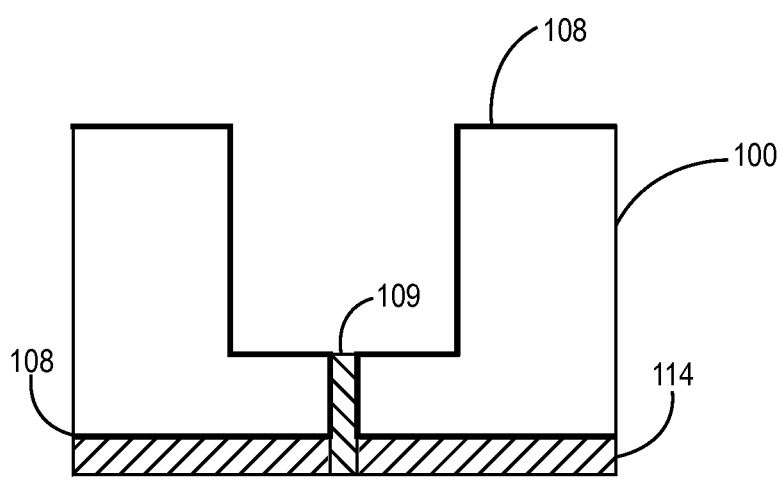
FIG. 2I depicts the feedthrough formed in the substrate after the holding device is removed.

During or after formation of insulative layer 108 over substrate 100 and the internal surface of aperture 106, a plating base 112 comprising a conductive material (e.g. metal such as the metal introduced into vias 106, 116, gold (Au) etc.) is introduced over the top surface of a temporary holder 110, as shown in FIG. 2D. A dielectric layer 114 (e.g. polyimide etc.) is then introduced in, for example, a liquid form that is spun coated or dip coated over plating base 112, as shown in FIG. 2E. Dielectric layer 114 creates a temporary bond between holder 110 and substrate 100. Thereafter, a via 116 is formed in dielectric layer 114 through an etching process, as depicted in FIG. 2F. Exemplary etching processes include a dry etch process (i.e. plasma), a wet etch process in which a photolithography step and photomask are included, and/or a direct writing method in which no mask is employed. Substrate 100 is temporarily coupled to dielectric layer 114, as shown in FIG. 2G. Conductive material is introduced into vias 106, 116 which forms feedthrough 109 as shown in FIG. 2H. Exemplary conductive material includes medical grade tantalum (Ta), niobium (Nb), titanium (Ti), platinum (Pt), gold (Au), alloys thereof, or other suitable biostable conductive material. The conductive material may be deposited into vias 106, 116 in a variety of ways such as through a plating operation, direct deposition or other suitable ways. In one embodiment, the conductive material is limited to metal that can be plated. Once feedthrough 109 is formed, temporary holder 108 and plating base 112 are separated or removed from second surface 104 as shown in FIG. 2I. To separate temporary holder 108 and plating base 112 from second surface 104, the adhesion force is reduced in the bond between temporary holder 108, plating base 112, and second surface 104 by increasing the ambient temperature around these components.

Figure 2J:
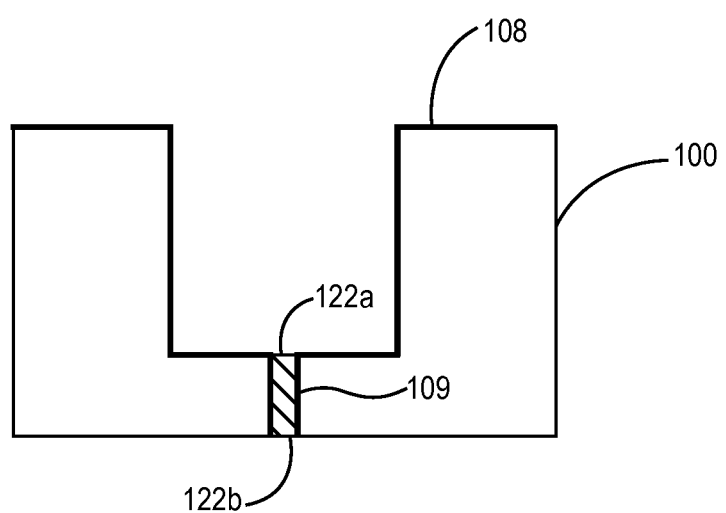
FIG. 2J depicts the feedthrough in the substrate after the dielectric layer is removed.
Figure 7:
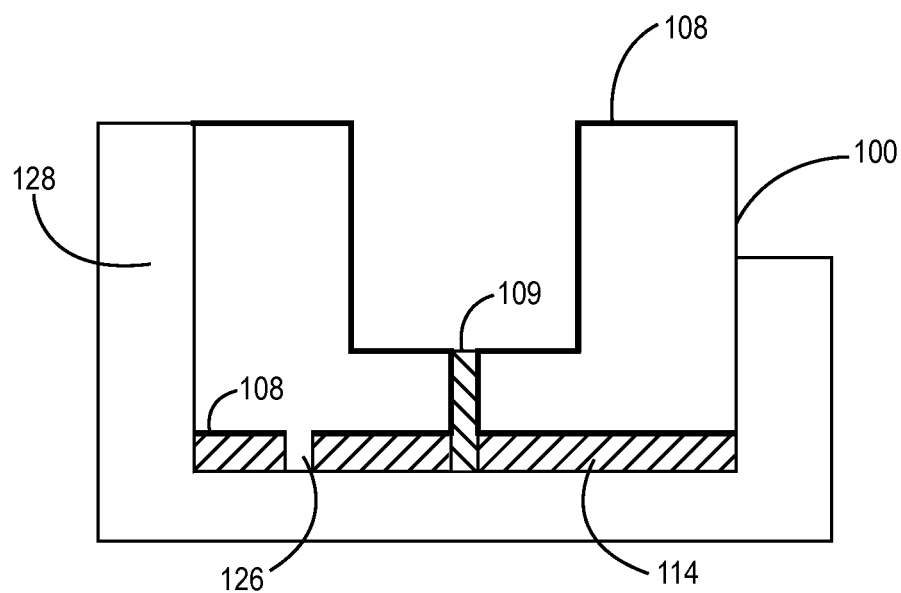
FIG. 7 depicts a schematic cross-sectional view of feedthrough formed in a substrate.

Thereafter, dielectric layer 114 and a portion of feedthrough 109 is removed through, for example, chemical mechanical polishing of dielectric layer 114, as depicted in FIG. 2J. As shown, feedthrough 109 is exposed after dielectric layer 114 is substantially or completely removed. After dielectric layer 114 is removed, feedthrough 109 is able to connect with an electronic component(s) or device(s) such that hermetically sealed electronic components directly connect with feedthrough 109 via end 122b and with other electronic components at end 122a. End 122b of feedthrough 109 could be electrically connected to electronic circuitry prior to or after formation of feedthrough 109. This side could be hermetically protected by a number of means such as through a dielectric layer, a metal layer, polymer layer, combinations or layer stacks 128 of those, or any other type of protection, as shown in another embodiment in FIG. 7. Dielectric layer 114 is either partially left from the previous operation or freshly applied after complete removal in the previous step. Via 126 provides access to circuitry (or other function) in substrate 100 at second surface 104 and that circuitry (or other function) and side 112b of feedthrough could be connected by any known way in the industry, since they will be protected by layer(s) 128. Feedthrough 109 does not have to extend through layer(s) 128. Specifically, layer 128 can be closed and provide optimal hermetic protection. The other end 122a of the feedthrough 109 could then be electrically connected in a biostable way to another electronic component or device.

Figure 3A:
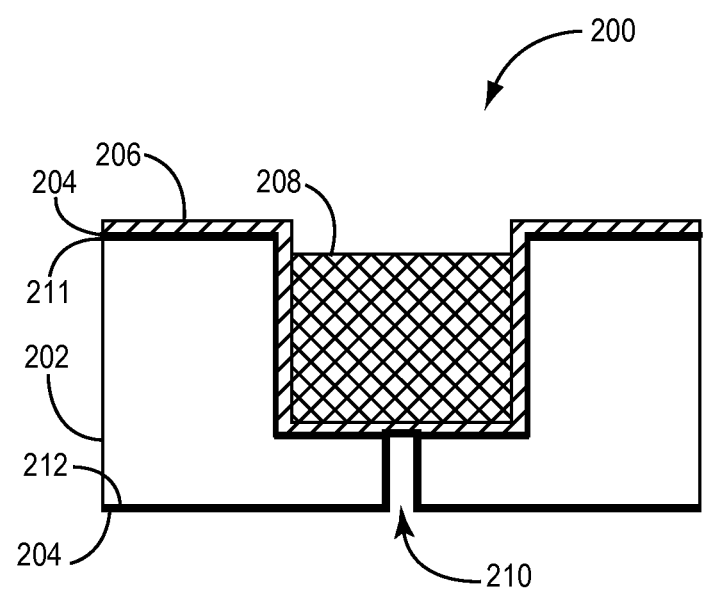
FIG. 3A depicts a schematic cross-sectional view of a substrate with a via formed therein.
Figure 3B:
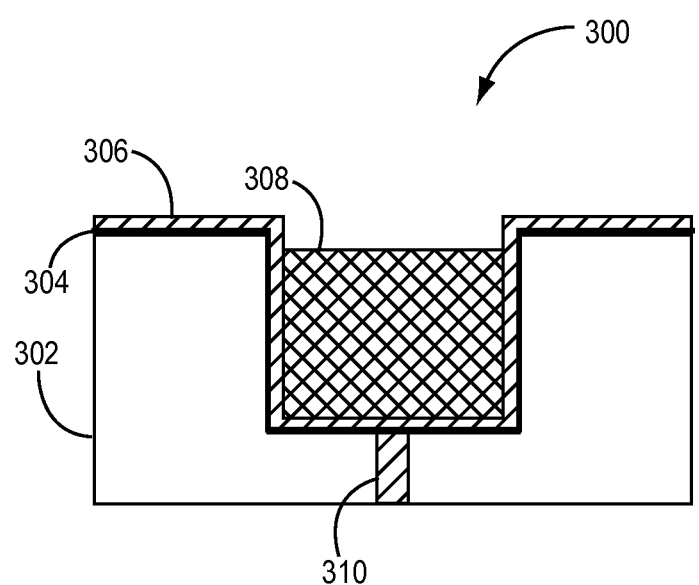
FIG. 3B depicts a schematic cross-sectional view of a feedthrough formed in the via of FIG. 3A.

Another embodiment for forming feedthrough 310 is depicted in FIGS. 3A through 3B. Device 200 comprises a substrate 202, a dielectric layer 204 (e.g. $SiO_2$), a conductive layer 206 (e.g. titanium etc.) with a conductive metal 208. Exemplary conductive material include a biostable conductive metal like Ta, Nb, Ti, Pt, Au, alloys thereof, or other suitable material. Conductive material could be a piece part which contacts the layer 206. Piece part does not indicate that the conductive material is large; rather, the conductive material does not necessarily have to be deposited over substrate 202. In this embodiment, DRIE is applied to one or both of first and second surfaces 211, 212 of substrate 202. A via 210 is formed on the second surface 212 of device 200. Conductive material is then introduced to via 210, which forms feedthrough 310 and electrically couples feedthrough 310 to conductive material 208. Exemplary conductive material includes Ta, Nb, Ti, Pt, Au, alloys thereof, or other biostable metal. The plating base 204 is then polished from the substrate 202.

Figure 4A:
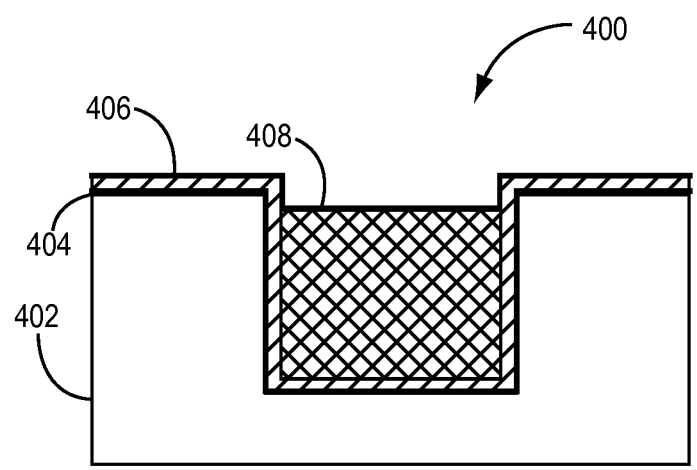
FIG. 4A depicts a schematic cross-sectional view of a substrate.
Figure 4B:
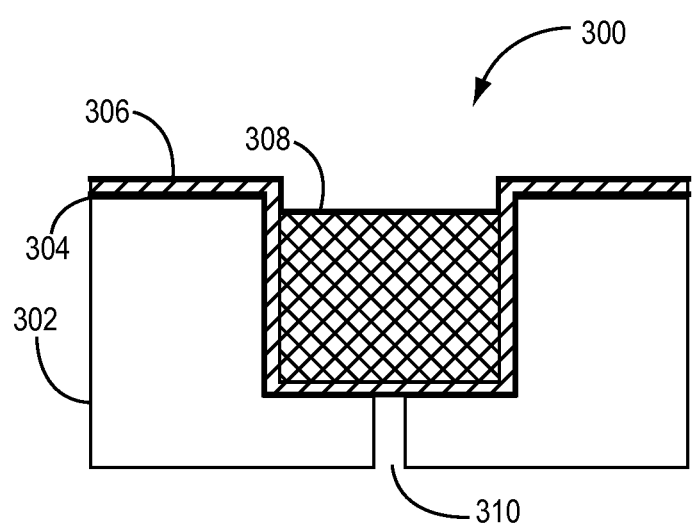
FIG. 4B depicts a via formed in the substrate of FIG. 4A.
Figure 4C:
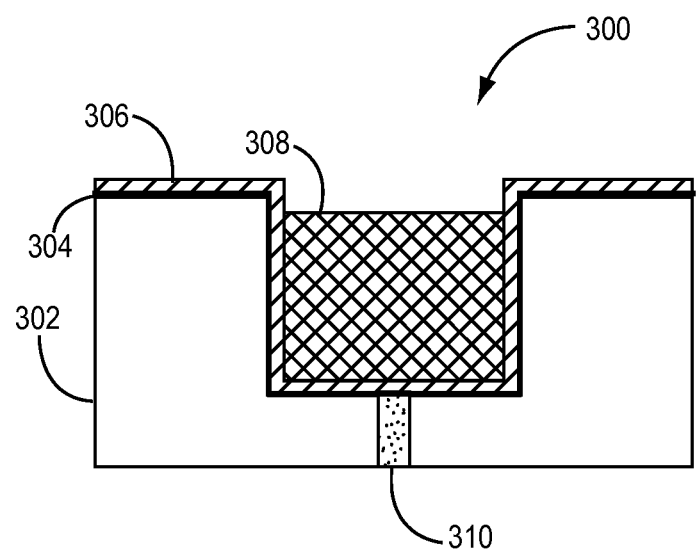
FIG. 4C depicts a feedthrough formed in the via of FIG. 4B.

Another embodiment for forming feedthrough 310 is depicted in FIGS. 4A through 4C. Device 400 comprises substrate 402, dielectric layer 404 (e.g. $SiO_2$), conductive layer 406 (e.g. titanium etc.) with conductive metal 408. In this embodiment, DRIE is applied to a back side 412 of substrate 402. Via 410 is formed on the back side of device 400 through etching. Conductive material is introduced to via 410, which forms feedthrough 312. Exemplary conductive material includes tantalum, niobium, titanium or other biostable metal material. The plating base 404 is removed from the substrate 402 through polishing such as through chemical mechanical polishing.

Figure 5:
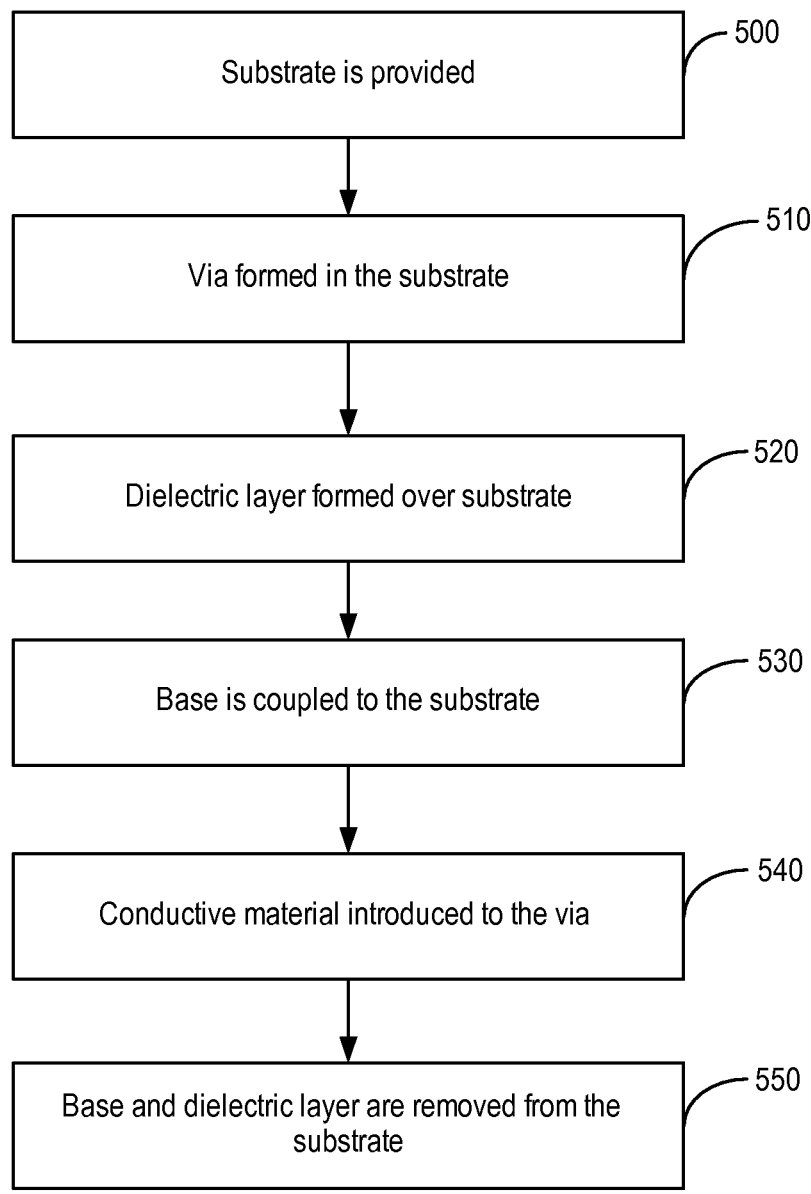
FIG. 5 is a flow diagram for forming a feedthrough in a substrate.

FIG. 5 is a flow diagram that depicts formation of a miniaturized feedthrough in a substrate. At block 500, a sensor substrate is provided. The sensor substrate includes a first and a second surface. At block 510, the sensor substrate includes a via that extends through the first and the second surfaces of the sensor substrate. At block 520, a dielectric layer is introduced or formed over a first surface of the sensor substrate. At block 530, a plating base is temporarily coupled to a first surface of the sensor substrate with the dielectric layer disposed between the first surface of the sensor substrate and the plating base. At block 540, conductive material is introduced to the via to form a feedthrough. At block 550, the plating base and dielectric layer are removed from the first surface of the sensor substrate.

Figure 6:
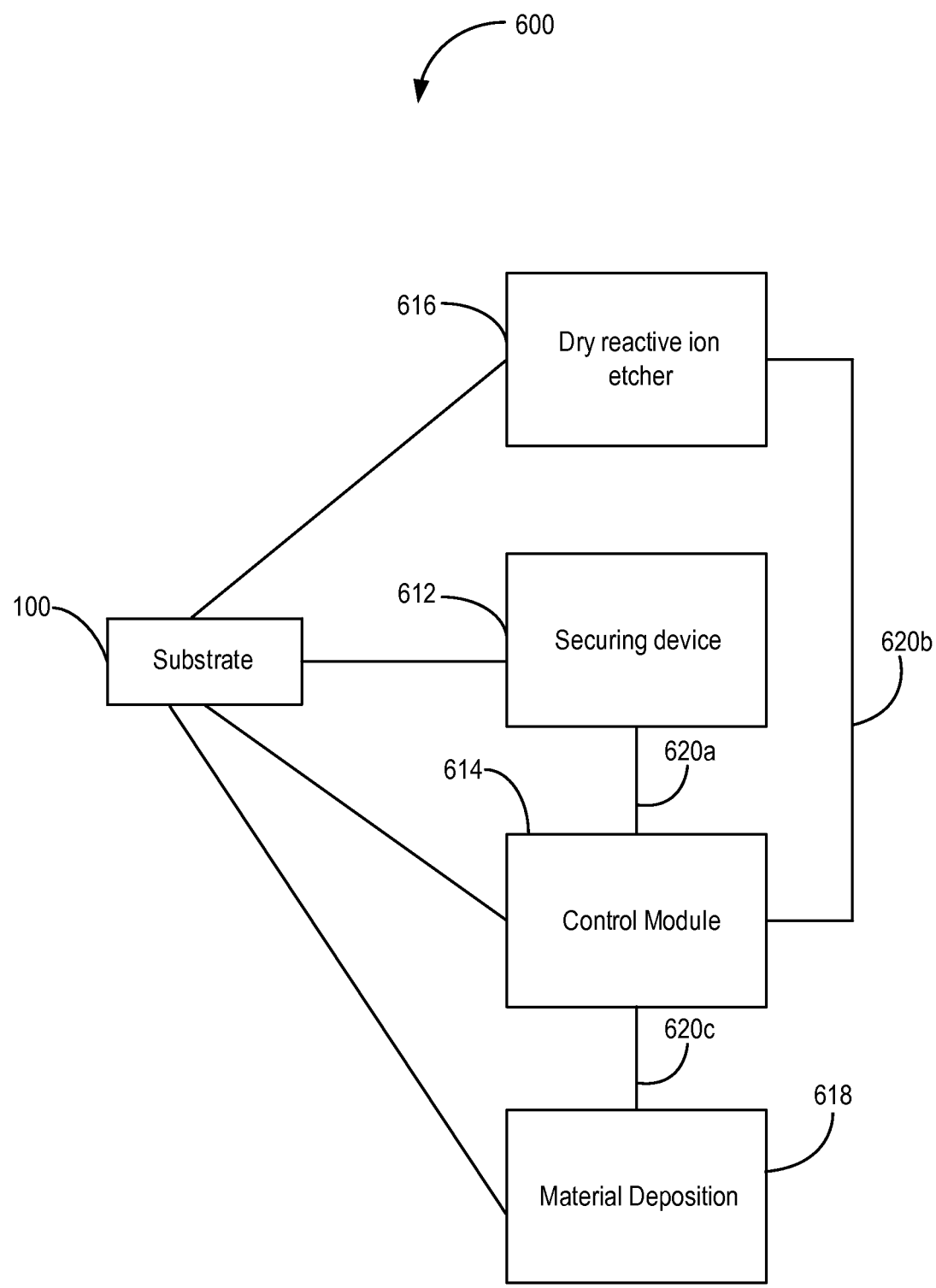
FIG. 6 is a feedthrough formation system for manufacturing a feedthrough in a substrate.

FIG. 6 depicts a feedthrough formation system 600. Feedthrough formation system 600 includes a control module 615, a securing device 612, a DRIE 616, and a material deposition device 618. Control module 615 is coupled wirelessly or hard-wired to a DRIE 616, material deposition device 618, and to securing device 612. Control module 615 is configured to send signals over buses 620 a-c (e.g. input/output buses) to these elements to automatically perform various functions described herein. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Securing device 612 completely or substantially immobilizes a sensor substrate 100 during assembly operations. Securing device 612 includes a holder 110, as previously described, and includes plating base 112, dielectric layer 114 and via 116, as shown FIG. 2F. Securing device 612 is configured to perform all of its functions associated with holding substrate 100 in place while operations are performed on substrate 100. Securing device 612 performs these functions, on an automatic basis, based upon signals received from control module 615. Securing device 612 optionally includes an actuator (not shown) for positioning or moving substrate 100 near or inside Material deposition device 618. Exemplary material deposition device 618 include a thermal oxidation chamber, a material deposition chamber or other suitable devices. The insulating layer is introduced over substrate 100 by material deposition device 618. DRIE 616 then etches one or more vias into substrate 100. After DRIE 616 has performed its operation on substrate 100, holder 110 is temporarily coupled to substrate 100. Thereafter, a conductive material is introduced to vias 106 and 116 by material deposition device 618 (also referred to as a conductive metal dispenser) or another type of device. Holder 110 is removed from substrate 100 and substrate 100 is polished. Feedthrough 109 is formed and available to electronically connect with an electronic device.

The present invention has numerous applications. For example, while the figures relate to unipolar feedthrough assemblies, other types of feedthrough assemblies may also rely on this process to reliable produce quality feedthrough assemblies. Additionally, the principles described herein can be extended to any number of trenches, given the size constraints associated with the substrate and/or the feedthrough. Trenches can also be replaced by holes instead to allow for the creation of a feedthrough island instead of merely forming a feedthrough pin. In another embodiment related to FIGS. 3A through 3B, feedthrough 310 is coupled to conductive metal when conductive layer 206 is not present, may involve deformation of a pin into a trench to make contact with the conductive material 208. A melted pool of conductive material couples the feedthrough 310 to the conductive material 208. Moreover, feedthroughs for implantable medical devices are used in a variety of ways. For example, feedthroughs are used in devices such as batteries, capacitors, sensors, implantable medical device housings, and other suitable devices or components.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. An implantable medical device (IMD) comprising:
a semiconductor substrate that includes a first surface and a second surface, and a via that extends through the first and the second surfaces, wherein the via comprises:
a first portion extending from the first surface into the substrate, and
a second portion extending from the second surface into the substrate to the first portion, wherein the width of the first portion is greater than the width of the second portion;
a dielectric layer formed over the first surface of the substrate and an interior surface of the first portion of the via; and
conductive material located within the second portion of the via and terminating at a junction between the first and second portions, wherein the junction is located between the first surface and the second surface, wherein the conductive material forms a feedthrough in the second portion of the via.

2. The IMD of claim 1 wherein the conductive material being one of tantalum (Ta), niobium (Nb), titanium (Ti), platinum (Pt), gold (Au), and alloys thereof.

3. The IMD of claim 1 wherein the first portion of the via includes a first inner diameter at the first surface and the second portion of the via includes a second inner diameter at the second surface, wherein the second inner diameter is smaller than the first inner diameter.

4. The IMD of claim 3, wherein the smaller second inner diameter reduces an aspect ratio of the via.

5. A method for forming a feedthrough for an implantable medical device comprising:
providing a semiconductor substrate with a first surface and a second surface, the substrate includes a via that extends through the first and the second surfaces, wherein the via comprises:
a first portion extending from the first surface into the substrate, and
a second portion extending from the second surface into the substrate to the first portion, wherein the width of the first portion is greater than the width of the second portion;
introducing a dielectric layer on the first surface of the substrate and an interior surface of the first portion of the via; and
introducing conductive material into the second portion of the via to form a feedthrough, wherein the conductive material in the second portion of the via terminates at a junction between the first and second portions, wherein the junction is located between the first surface and the second surface.

6. The method of claim 5 wherein the semiconductor substrate is a sensor substrate.

7. The method of claim 5 further comprising:
coupling a base to the second surface of the substrate with dielectric material disposed between the second surface of the substrate and the base.

8. The method of claim 7 further comprising:
removing the base and dielectric material from the second surface of the substrate.

9. The method of claim 5 wherein the conductive material being one of Nb, Ti, Pt, Au, and alloys thereof.

10. A method for forming a feedthrough associated with an implantable medical device, the method comprising:
providing a semiconductor substrate which includes a first surface and a second surface;

creating a first via in the substrate, wherein the first via extends into the substrate from the first surface;

creating a second via in the substrate, the second via in communication with the first via, wherein the second via extends into the substrate from the second surface, wherein the width of the first via is greater than the width of the second via; and forming a feedthrough in the second via by introducing conductive material into the second via, wherein the conductive material terminates at a junction between the first and second vias, wherein the junction is located between the first surface and the second surface.

11. The method of claim 10, wherein the conductive material being one of Ta, Nb, Ti, Pt, Au, and alloys thereof.

12. The method of claim 10, wherein the method further comprises forming a dielectric layer on the first surface and an interior surface of the first via.

13. The method of claim 12, wherein the method further comprises forming a conductive layer on the dielectric layer, wherein the conductive material is electrically coupled to the conductive layer.

14. The method of claim 13, wherein the method further comprises forming conductive metal in the conductive layer within the first via.

15. The method of claim 10, wherein creating the first via comprises forming a trench in the first surface of the substrate.

16. The method of claim 15, wherein the method further comprises locating a metal pin in the trench to electrically couple the metal pin to the conductive material.

17. The method of claim 10, wherein the height of the first via is greater than the height of the second via.

18. The method of claim 10, wherein the method further comprises forming one or more layers on the second surface of the substrate, wherein the one or more layers comprise at least one hermetically-seated electronic device.

19. An implantable medical device (IMD) comprising:
a semiconductor substrate comprising a first surface and a second surface;
a first aperture extending from the first surface into the substrate;
a second aperture extending from the second surface into the substrate to the first aperture, wherein the width of the first aperture is greater than the width of the second aperture;
a dielectric layer on the first surface and an interior surface of the first aperture;
a conductive layer on the dielectric layer; and
a feedthrough comprising conductive material within the second aperture, wherein the conductive material terminates at a junction between the first and second apertures, wherein the junction is located between the first surface and the second surface wherein the conductive material in the second aperture is electrically coupled to the conductive layer.

20. The IMD of claim 19, wherein the first aperture comprises a trench.

21. The IMD of claim 20, wherein a metal pin is located in the trench.

22. The IMD of claim 19, wherein conductive metal is located within the first aperture on the conductive layer, wherein the conductive metal is electrically coupled to the conductive layer.

23. The IMD of claim 19, wherein the height of the first aperture is greater than the height of the second aperture.

24. The IMD of claim 19, wherein the IMD further comprises one or more layers on the second surface forming at least one hermetically-sealed electronic device.

25. An implantable medical device (IMD) comprising:
a semiconductor substrate that includes a first surface and a second surface, and a via that extends through the first and the second surfaces, wherein the via comprises:
a first portion extending from the first surface into the substrate, and
a second portion extending from the second surface into the substrate to the first portion, wherein the width of the first portion is greater than the width of the second portion;
a dielectric layer formed directly onto the first surface of the substrate and an interior surface of the first portion of the via; and
conductive material located within the second portion of the via and terminating at a junction between the first and second portions, wherein the junction is located between the first surface and the second surface, wherein the conductive material forms a feed through in the second portion of the via.

* * * * *